(12) United States Patent
Alzate et al.

(10) Patent No.: US 10,726,944 B2
(45) Date of Patent: Jul. 28, 2020

(54) RECOMMENDING NOVEL REACTANTS TO SYNTHESIZE CHEMICAL PRODUCTS

(71) Applicant: International Business Machines Corporation, Armonk, NY (US)

(72) Inventors: Carlos Alzate, Dublin (IE); Beat Buesser, Dublin (IE); Ernesto Diaz-Aviles, Dublin (IE); Akihiro Kishimoto, Dublin (IE); John Savage, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 944 days.

(21) Appl. No.: 15/284,612

(22) Filed: Oct. 4, 2016

(65) Prior Publication Data

US 2018/0096100 A1    Apr. 5, 2018

(51) Int. Cl.
*G06N 5/00*    (2006.01)
*G16B 40/00*    (2019.01)
(Continued)

(52) U.S. Cl.
CPC ......... *G16B 40/00* (2019.02); *G06F 16/9024* (2019.01); *G16C 20/10* (2019.02)

(58) Field of Classification Search
CPC .................. G06F 16/9024; G16C 20/10
See application file for complete search history.

(56) References Cited

U.S. PATENT DOCUMENTS 5,858,670 A    1/1999 Lam et al.
5,862,514 A    1/1999 Huse et al.
(Continued)

FOREIGN PATENT DOCUMENTS

WO    2006/068827 A1    6/2006
WO    2008/157504 A1    12/2008

OTHER PUBLICATIONS

"Computer-Assisted Synthetic Planning: The End of the Beginning," Sara Szymkuć et al. Chem. Int. Ed. 2016, 55, 5904-5937, DOI : 10.1002/anie.201506101, first published Apr. 8, 2016 (Year: 2016).*
(Continued)

*Primary Examiner* — Hal Schnee
(74) *Attorney, Agent, or Firm* — Scully, Scott, Murphy & Presser, P.C.; Rabin Bhattacharya

(57) ABSTRACT

A method is provided for determining at least one candidate reactant. One embodiment of this method includes the following steps: forming by a computer processor a graph of known reactants and known products, the graph comprising links between the known reactants and their known products, receiving by a computer processor the target compound, determining by a computer processor whether the graph includes the target compound and adding the target compound to the graph if the target compound was not previously included, forming by a computer processor a matrix representing at least a portion of the known reactants, a portion of the known products and the target compound, providing a matrix value of the graph by a computer processor for one or more candidate reactants and determining by a computer processor at least one link in the graph between the target compound and the candidate reactant based on matrix values.

13 Claims, 8 Drawing Sheets

(51) Int. Cl.
 *G06F 16/901* (2019.01)
 *G16C 20/10* (2019.01)

(56) References Cited

U.S. PATENT DOCUMENTS

| | | | |
|---|---|---|---|
| 5,871,924 | A | 2/1999 | Yarus et al. |
| 6,245,937 | B1 | 6/2001 | Cheng et al. |
| 6,495,824 | B1 | 12/2002 | Atkinson |
| 6,571,226 | B1 | 5/2003 | Mydlowec et al. |
| 6,753,449 | B2 | 6/2004 | Guo |
| 6,859,735 | B1 | 2/2005 | Stoughton et al. |
| 7,250,950 | B2 | 7/2007 | Smith et al. |
| 7,751,988 | B2 | 7/2010 | Kita et al. |
| 8,140,267 | B2 | 3/2012 | Boyer et al. |
| 2002/0049548 | A1 | 4/2002 | Bunin |
| 2002/0087275 | A1 | 7/2002 | Kim et al. |
| 2002/0111782 | A1 | 8/2002 | Klaffke et al. |
| 2003/0087334 | A1 | 5/2003 | Bunin et al. |
| 2005/0124002 | A1 | 6/2005 | Cardozo et al. |
| 2010/0225650 | A1 | 9/2010 | Grzybowski et al. |
| 2014/0172387 | A1 | 6/2014 | Ford |
| 2015/0269356 | A1* | 9/2015 | Pallai ............... C07D 405/04 506/8 |
| 2016/0012088 | A1* | 1/2016 | Rossi ............... G06Q 30/02 707/736 |
| 2016/0283677 | A1* | 9/2016 | Carmeli ............ G16H 50/50 |
| 2017/0140382 | A1* | 5/2017 | Chari ............... G06Q 20/4016 |

OTHER PUBLICATIONS

Bishop K.J.M. et al., "The Core and Most Useful Molecules in Organic Chemistry", Angew. Chem. Int. Ed. 45:5348-5354 (2006).
Fialkowski M. et al., "Architecture and Evolution of Organic Chemistry", Angew. Chem. Int. Ed. 44:7263-7269 (2005).
Fuller P.E. et al., "Chemical Network Algorithms for the Risk Assessment and Management of Chemical Treats", Angew. Chem. 124:8057-8061 (2012).
Gothard C.M. et al., "Rewiring Chemistry: Algorithmic Discovery and Experimental Validation of One-Pot Reactions in the Network of Organic Chemistry", Angew. Chem. Int. Ed. 51:722-7927 (2012).
Heifets A. et al., "Construction of New Medicines via Game Proof Search", Proceedings of the Twenty-Sixth AAAI Conference on Artificial Intelligence, pp. 1564-1570 (2012).
Koren Y., "Matrix Factorization Techniques for Recommender Systems", IEEE Computer Society, pp. 42-49 (Aug. 2009).
Kowalczyk B. et al., "Sythetic Popularity Reflects Chemical Reactivity", Journal of Physical Organic Chemistry 22:897-902 (2009).
Kowalik M. et al., "Parallel Optimization of Synthetic Pathways Within the Network of Organic Chemistry", Angew. Chem. Int. Ed. 51:7928-7932 (2012).
Law J. et al., "Route Designer: A Retrosynthetic Analysis Tool Utilizing Automated Retrosynthetic Rule Generation", J. Chem. Inf. Model. 49(3):593-602 (2009).
Liben-Nowell D. et al., "The Link-Prediction Problem for Social Networks", pp. 1-23 (2003, 2007).
Mell P., et al., "The NIST Definition of Cloud Computing", NIST Special Publication 800-145, National Institute of Standards and Technology, U.S. Department of Commerce, pp. 1-7 (Sep. 2011).
Menon A.K. et al., "Link Prediction via Matrix Factorization", LNAI 6912:437-452 (2011).
Soh S. et al., "Estimating Chemical Reactivity and Cross-Influence from Collective Chemical Knowledge", Chem. Sci. 3:1497-1502 (2012).
Yamanishi Y. et al., "Supervised Enzyme Network Inference from the Integration of Genomic Data and Chemical Information", Bioinformatics 21(1):i468-i477 (2005).

* cited by examiner

FIG. 3

RECOMMENDING NOVEL REACTANTS TO SYNTHESIZE CHEMICAL PRODUCTS

FIELD

The present application relates generally to computers, and computer applications, and more particularly to computer-implemented methods to provide novel chemical reactants for synthesizing chemical products.

BACKGROUND

Creating new chemical compounds is part of several industries, including the pharmaceutical, chemical, material and food industries. When forming new chemical compounds typically researchers solve what is needed for the reaction manually by designing a target chemical compound and attempting to determine what the set of required reactants are to form a pathway for generating the target. This is a time-consuming task that can contain human error such as failing to determine solutions or finding only suboptimal ones.

Although databases exist to provide reactants for a desired compound, these databases only exist for existing compounds, not new compounds. Also, software is available that can perform retro-synthetic analysis for finding pathways and reactants, but this software is computationally demanding due to combinatorial complexity of their search-based approaches. Also, this software requires reaction rules defined by reaction examples in existing literature.

BRIEF SUMMARY

A method is provided for determining at least one candidate reactant that can be used to synthesize a new target compound.

One embodiment of this method includes the following steps: forming by a computer processor a graph of known reactants and known products, the graph comprising links between the known reactants and their known products, receiving by a computer processor the target compound, determining by a computer processor whether the graph includes the target compound and adding the target compound to the graph if the target compound was not previously included, forming by a computer processor a matrix representing at least a portion of the known reactants, a portion of the known products and the target compound, providing a matrix value of the graph by a computer processor for one or more candidate reactants and determining by a computer processor at least one link in the graph between the target compound and the candidate reactant based on matrix values.

A system that includes one or more hardware processors operable to perform one or more methods described herein also may be provided.

A computer readable storage medium storing a program of instructions executable by a machine to perform one or more methods described herein also may be provided.

Further features as well as the structure and operation of various embodiments are described in detail below with reference to the accompanying drawings. In the drawings, like reference numbers indicate identical or functionally similar elements.

BRIEF DESCRIPTION OF THE SEVERAL VIEWS OF THE DRAWINGS

FIG. 3 is a graphical representation of two matrices providing values for several reactants and products;

DETAILED DESCRIPTION

The disclosure is directed to a computer system and computer-implemented method to recommend candidate reactants that can be used to synthesize new target compounds. The system and method are used to determine which possible reactants can be utilized to synthesize an inputted structure of a new target compound.

The disclosed computer system and computer-implemented method is configured to provide recommended candidate reactants in a relatively short time frame for relatively simple to relatively complex target compounds.

Presently, the entire chemical reaction network could be represented as a graph where links between compounds represent reactions between them. The graph of known chemical reactions is incomplete because of the very high combinatorial complexity of atoms and bonds. Therefore, the disclosed computer system and computer-implemented method is configured to predict links in a graph of a chemical reaction network, thereby extending the incomplete graph.

The disclosed computer system and computer-implemented method is configured to operate in two phases—the preprocessing phase and the query phase.

In the preprocessing phase the disclosed computer system and computer-implemented method is configured to create a model that predicts links between compounds of a number of reactions. In the query phase the disclosed computer system and computer-implemented method is configured to predict at least one link to a target compound queried by a user and provide at least one candidate reactant calculated by the predicted link. These two phases are further discussed below.

Figure 1:
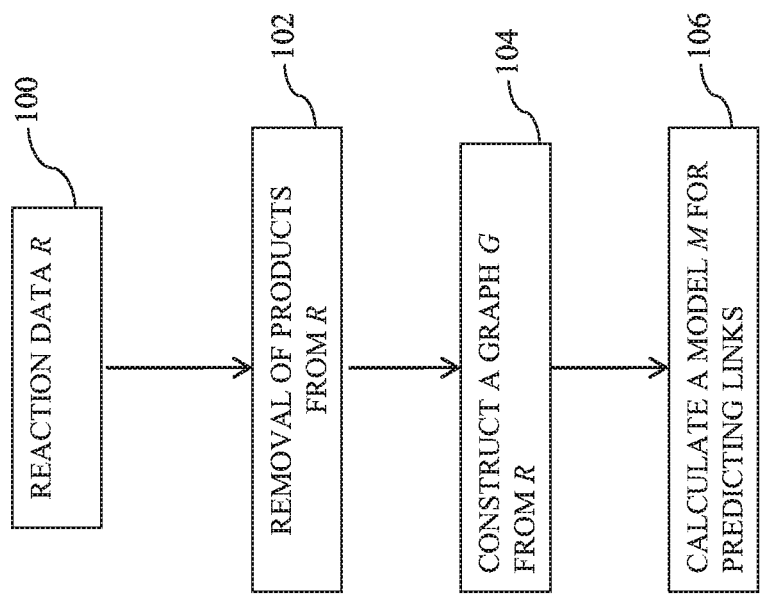
FIG. 1 is a flow diagram illustrating a method of preprocessing.

FIG. 1 depicts a flow diagram of the preprocessing phase. Although not shown this flow diagram is occurring as part of one or more modules of one or more hardware processors. In particular, FIG. 1 illustrates the receipt of reaction data 100. Reaction data 100 can include a plurality of known chemical reactants and products (reaction set), one example of which is $2H_2+O_2 \rightarrow 2H_2O$ (A+B→C). Reaction data 100 can include tens, hundreds, thousands, etc. of known reaction sets.

After all reaction data 100 is received, a number of products are optionally removed from the reaction sets in step 102. For example if a received reaction step in reaction data 100 was A+B→C+D, and D qualified for removal, the received set of reaction data 100 would be modified in step 102 to remove D so that the new reaction set in step 102 is A+B→C. In this example D can qualify for removal in one or more of several ways, such as D has a structure below a threshold molecular size and/or molecular weight or D is a common product (such as H₂O).

Figure 2:
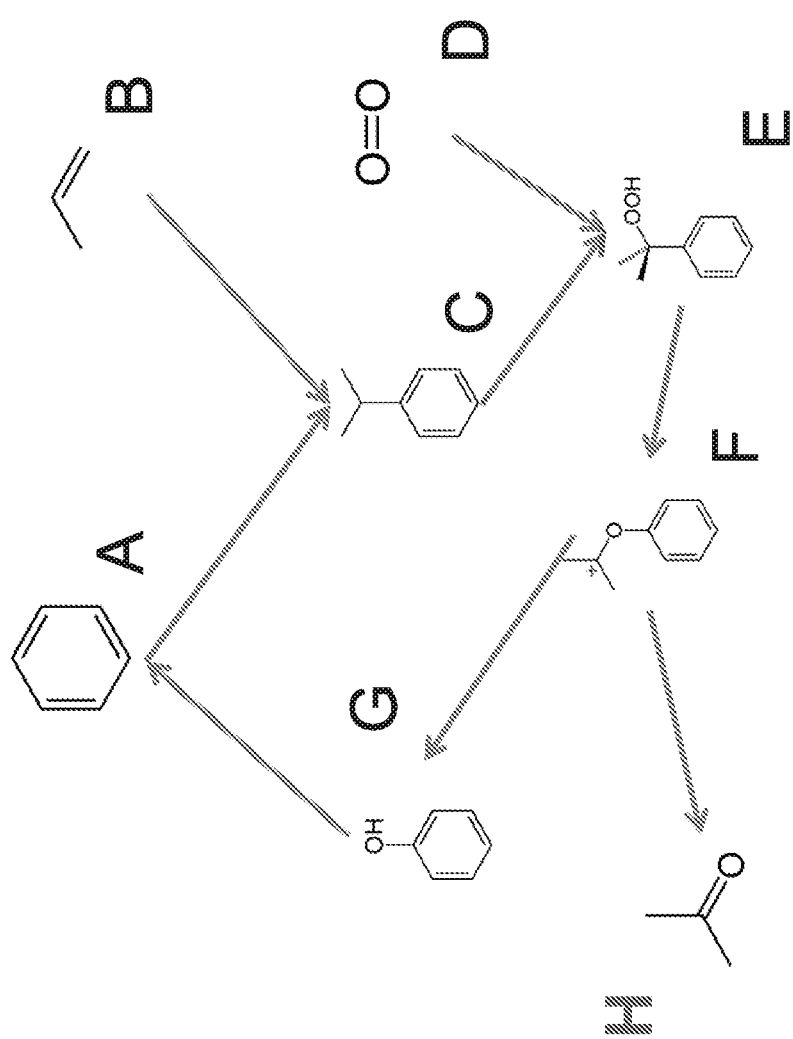
FIG. 2 is a graphical representation of a number of reactants and products.

From step 102, the new reaction sets are used to construct a graph G in step 104. An example of a graph is shown in FIG. 2. As can be seen from FIG. 2, a number of known reaction sets from step 104 form a graph with interweaved products and reactants. In the example of FIG. 2, the reactants (A and B) react to form a product (C), with reactants (C and D) reacting to form another product (E). As can be seen other products that were removed in step 102 are not shown in this graph. Also this graph is small for exemplary purposes, in step 104 the graph formed could be much larger. In this example, product H is the target compound.

After a graph is constructed in step 104, a model is calculated to predict other reactants for products in the graph. To form this model, machine learning algorithms for recommender systems can be used. The graph is regarded as an embodiment of the memory-efficient matrix representation of the recommender system. Edges in the graph correspond to examples of the previously known reactions. By using the graph as a training example, machine learning algorithms learn some principles about interactions between products and reactions, thus forming a model. Then, the formed model predicts the new edges that are not currently present in the graph due to the fact that the chemists have not yet discovered such reactions. Step 106 can also be considered a training phase during which the model is more robustly created and accurate links are predicted.

Figure 3:
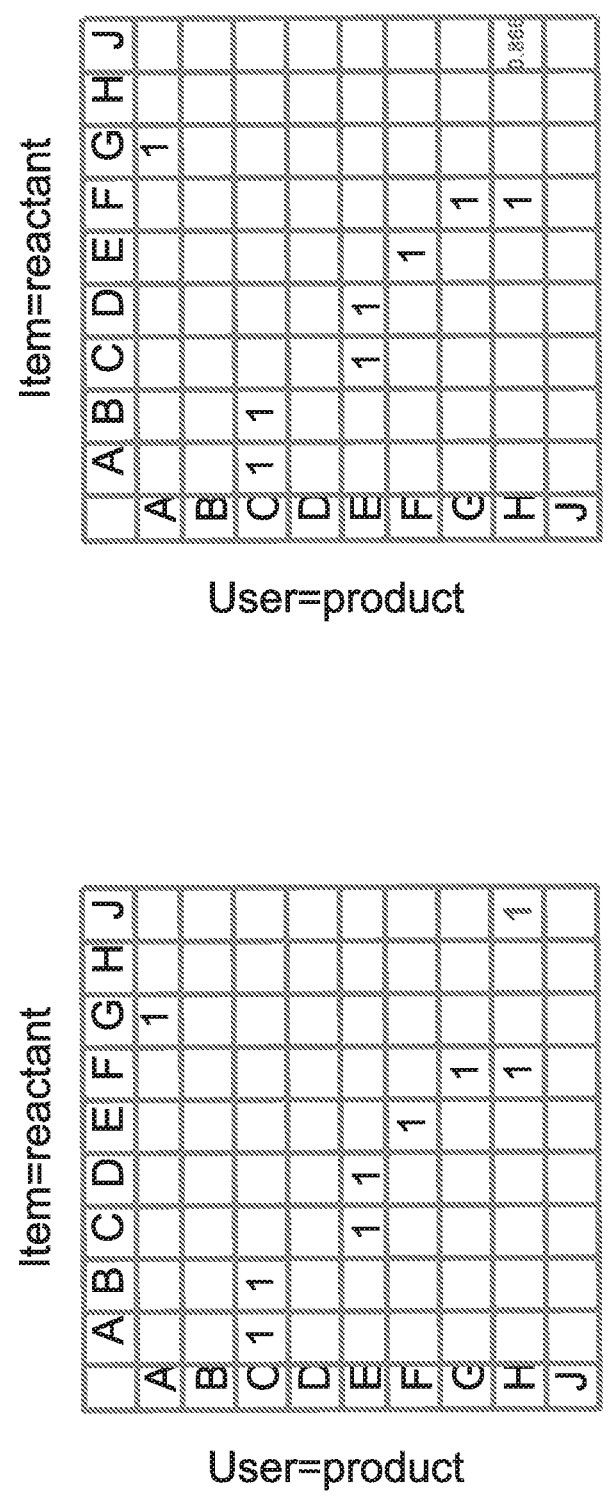

In step 106 the nodes of the created graph are considered as both "users" and "items" as those terms are used in recommender systems. The "items" or reactants, and the "users" or the product can be used to form a matrix as shown in FIG. 3. As can be seen reactants A and B result in product C, therefore, column A row C and column B row C each receive a 1 value. The formation of the matrix continues for each reactant and product of the graph and can be much larger than what is shown in FIG. 3. In practice, as an efficient embodiment, the graph structure generated in step 104 can be used to represent the matrix. The value of "1" in FIG. 3. except in the cell of row H column J indicates that there is a link between two nodes in the graph. If there is no link in the graph, its corresponding matrix entries has value 0. The formed model attempts to predict that the value in row H column J is 1, indicating that J is a reactant to produce H.

Using a suitable matrix method for providing matrix values, such as but not limited to factorization, vectors representing the latent features of products and reactants learned in step 106 can be used to calculate each value in the matrix. The dot product of these calculated vectors can be used to recommend further reactants for a target compound. For example, in FIG. 3, in this embodiment assume that the basic matrix factorization algorithm uses a two-dimensional normalized vector for each product/reactant, and the vectors for product H and reactant J are (0.5, 0.866) and (0.866, 0.5), respectively. Additionally, assume that the value of the dot product ranges between 0 and 1, and the larger the dot product value is, the higher the chance of having a link in the graph is. The dot product of the vectors of product H and reactant J is 0.5×0.866+0.866×0.5=0.866 (as shown in the matrix on the right of FIG. 3). Since the value of 0.866 is closer to 1 than 0, J is highly recommended as a reactant for product H (shown as value 1 in the matrix on the left of FIG. 3). To improve accuracy of recommendation, other algorithm variants of matrix factorization such as Bayesian Personalized Ranking (BPR) and factorization machines or even other machine learning algorithms can be used as possible embodiments.

As noted above the disclosed computer system and computer-implemented method is configured to operate in two phases—the preprocessing phase and the query phase, with the preprocessing phase discussed above. The query phase is now discussed and shown in FIG. 4.

In the query phase a query is received regarding a target compound in step 202, which would include the structure of that target compound. This query could be provided by a user who is attempting to determine a candidate reactant. For exemplary purposes the target compound can be referred to as "H".

Once the target compound is received, the graph formed in the preprocessing phase is checked to determine if the target compound is already in the graph in step 204. If the target compound is not already in the graph, the target compound is added to the graph in step 206 and the process proceeds to step 208. If the target compound is already in the graph, the process proceeds to step 208, which predicts at least one link, or candidate reactant, for the target compound. Step 208 utilizes the model M from step 106 along with a matrix factorization discussed in reference to FIG. 3 to provide a candidate reactant as shown in FIG. 4.

Figure 5:
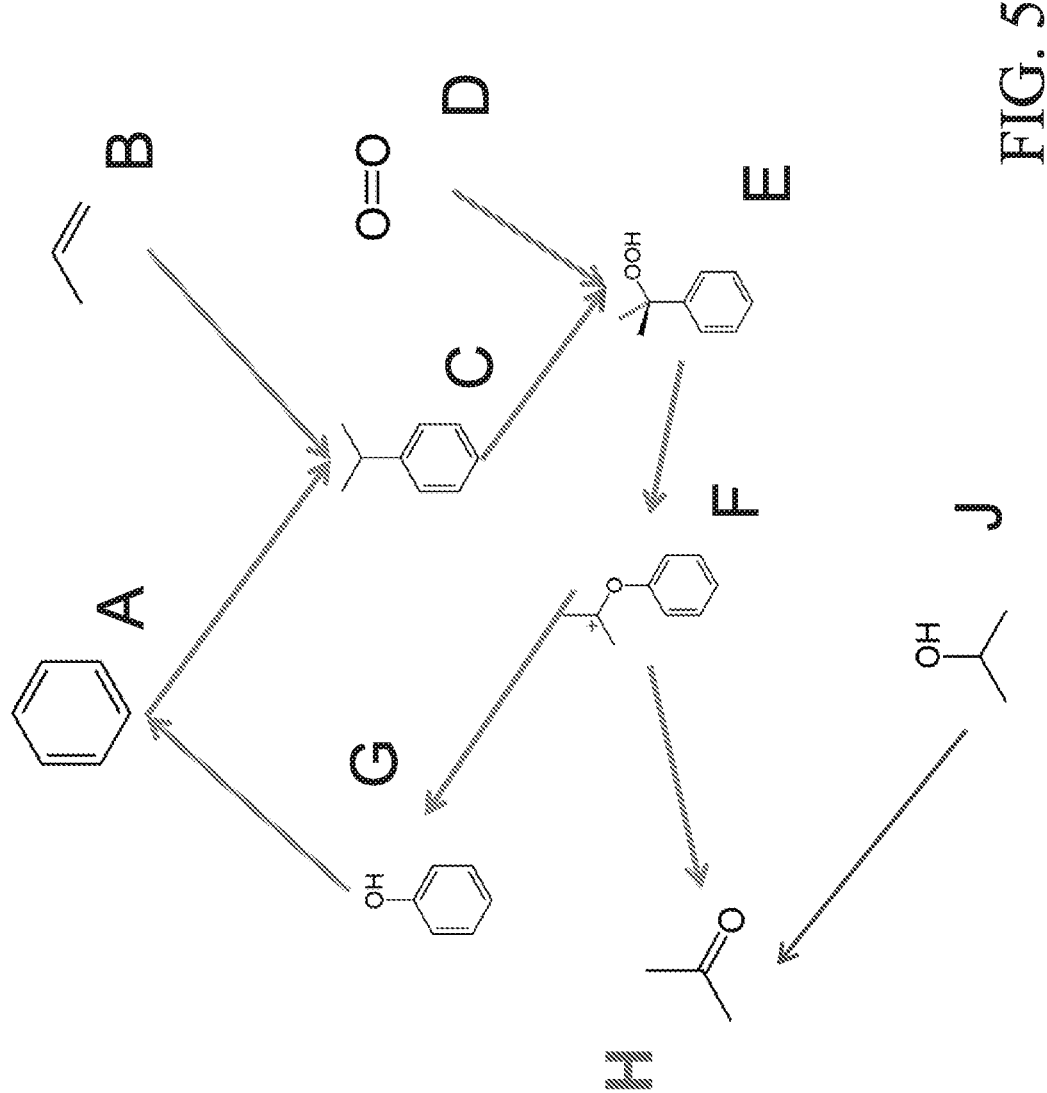
FIG. 5 is a graphical representation of a number of reactants and products.

As can be seen in the graph of FIG. 5, a reactant that was not present in FIG. 2 was determined, in this example reactant "J". Based on this predicted candidate reactant a user can then attempt to synthesize the target compound—by for example reacting reactants "F" and 'T' from FIG. 5 to form target compound "H".

Figure 4:
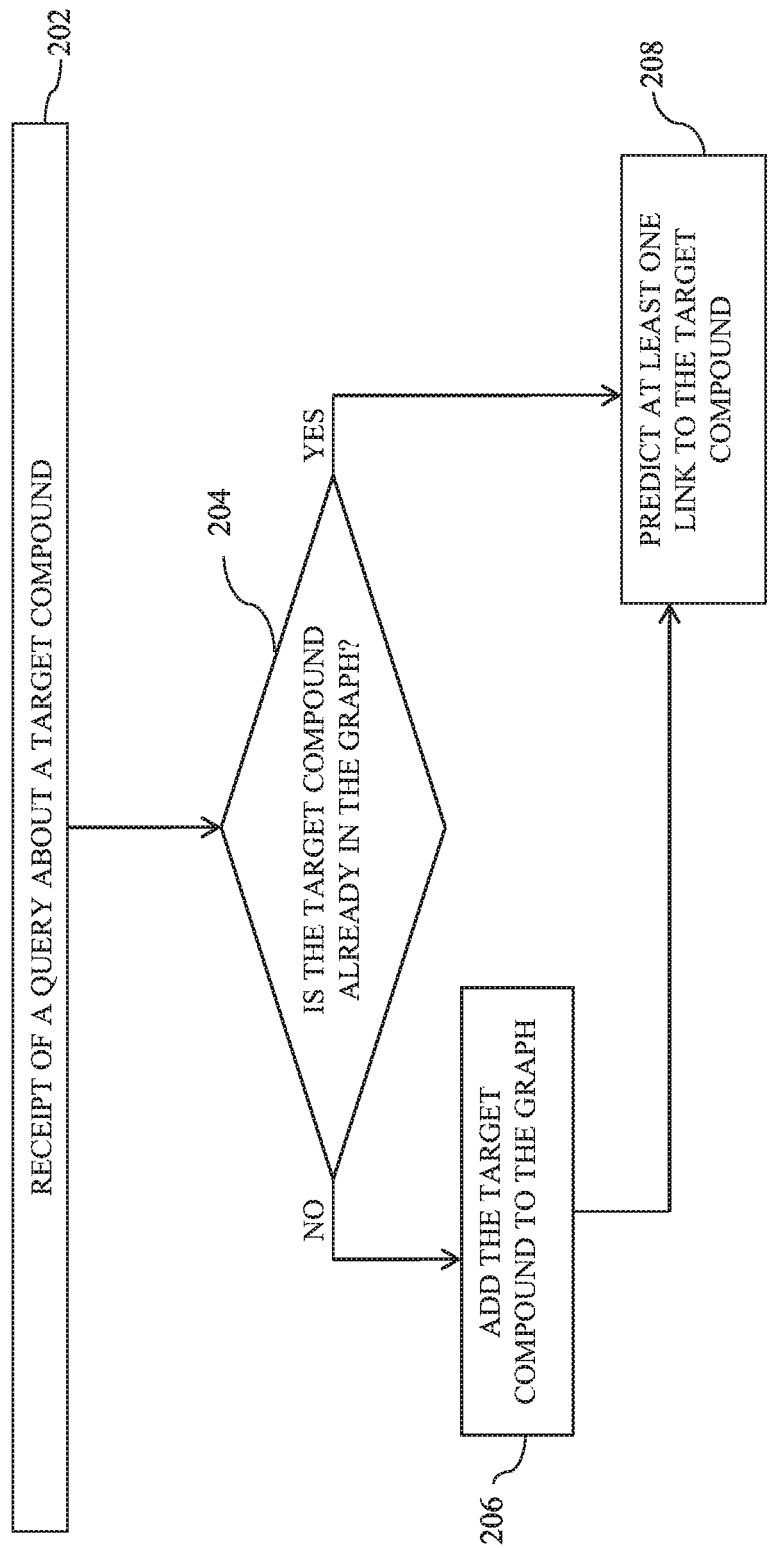
FIG. 4 is a flow diagram of a method of querying a reactant.

The method steps of FIG. 4 can be repeated one or more times to produce other candidate reactants, as desired. Also, the method steps of FIG. 4 can produce a number of ranked candidate reactants based on their predicted values.

To increase accuracy, fingerprints of candidate reactants can optionally be included to modify the values of the "items" columns of the matrix of FIG. 3. These fingerprints can increase efficiency by providing a higher value to reactants that are more similar to a target compound.

For example these fingerprints can be structurally based so that more structurally similar reactants are given a higher value in the matrix. As one example of this if the target compound were OC=CN, candidate reactants such as C=CN, N**O, C=C, C—O, C—N, N and O can be given higher values than other reactants in the matrix.

As another example, these fingerprints can be pattern based, so that reactants that have a more similar pattern to the target compound are given a higher value in the matrix. As one example of this if the target compound were OC=CN, candidate reactants having 0-bond paths (C, O, N), having 1-bond paths (OC, C=C, CN), having 2-bond paths (OC=C, C=CN) and having 3-bond paths (OC=CN) can be given higher values than other reactants in the matrix. Also optionally the binary vectors produced for each candidate reactant can be compared in the matrix using distance criteria to give a similarity score to the target compound.

This modification of the factor vector using molecular fingerprints can also be learned by the model in step 106.

Further, in step 202 in the method of FIG. 4, a portion or portions of a target compound (such as a fingerprint or a partial fingerprint of a target compound) can be received instead of a complete structure. In this example the portion or portions of the target compound can be included in the graph in step 206 if they are not already present or step and at least one link can be predicted for the portion or portions of the target compound. Similarly, as an embodiment of steps 100-106, the portion or portions of the compounds can be used to generate the graph and form the model.

In another embodiment, the values in the matrix of FIG. 3 can also be modified based on other constraints other than chemical attributes. For example, these values can be modified based on availability of the reactants, costs of the reactant, reaction speed of the reactant, thermodynamic properties of the reactant, toxicity of the reactant, biological activity of the reactant. In other embodiments other modifications can be made to matrix values.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure that includes a network of interconnected nodes.

Figure 6:
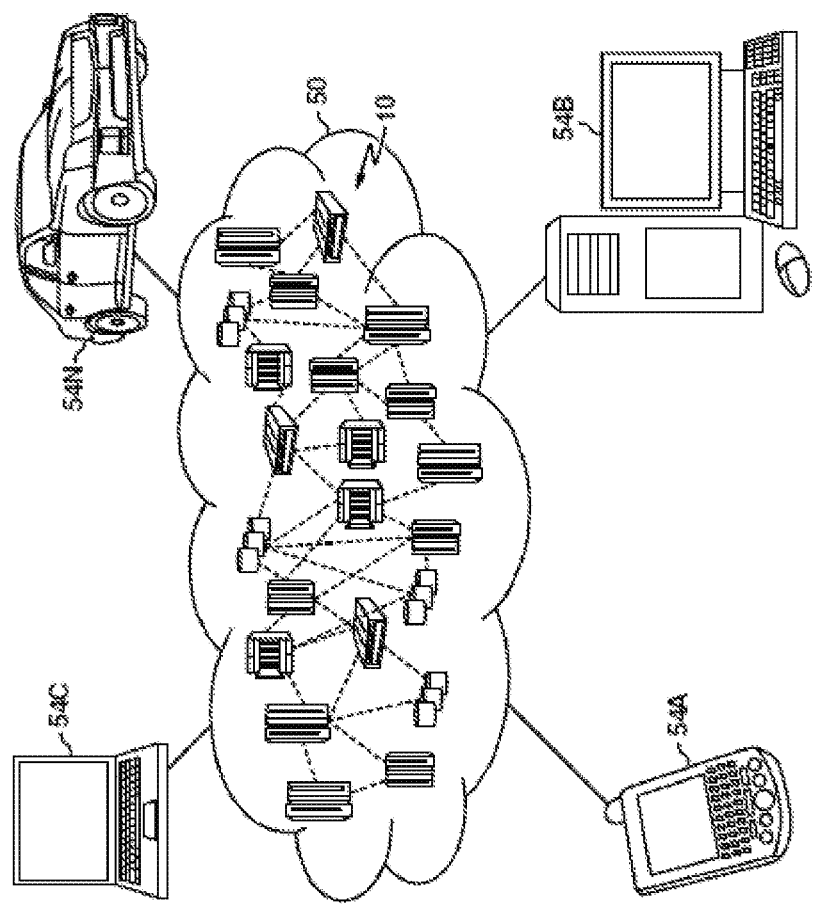
FIG. 6 depicts a cloud computing environment according to an embodiment of the present invention.

Referring now to FIG. 6, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
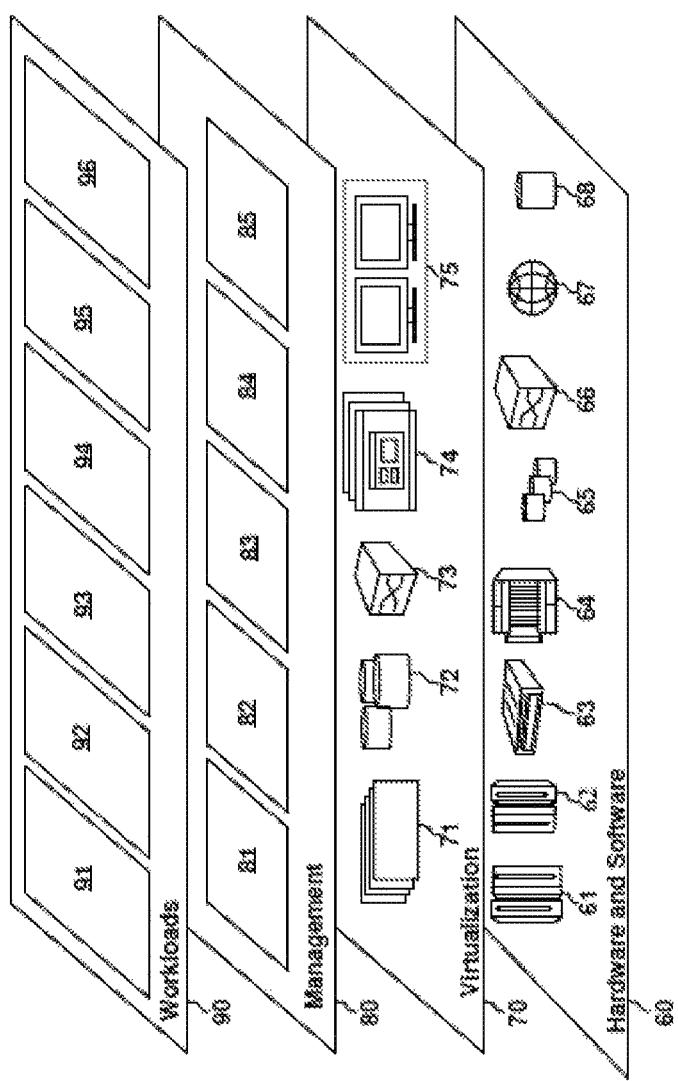
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and recommending novel chemical reactants for synthesizing chemical products 96.

Figure 8:
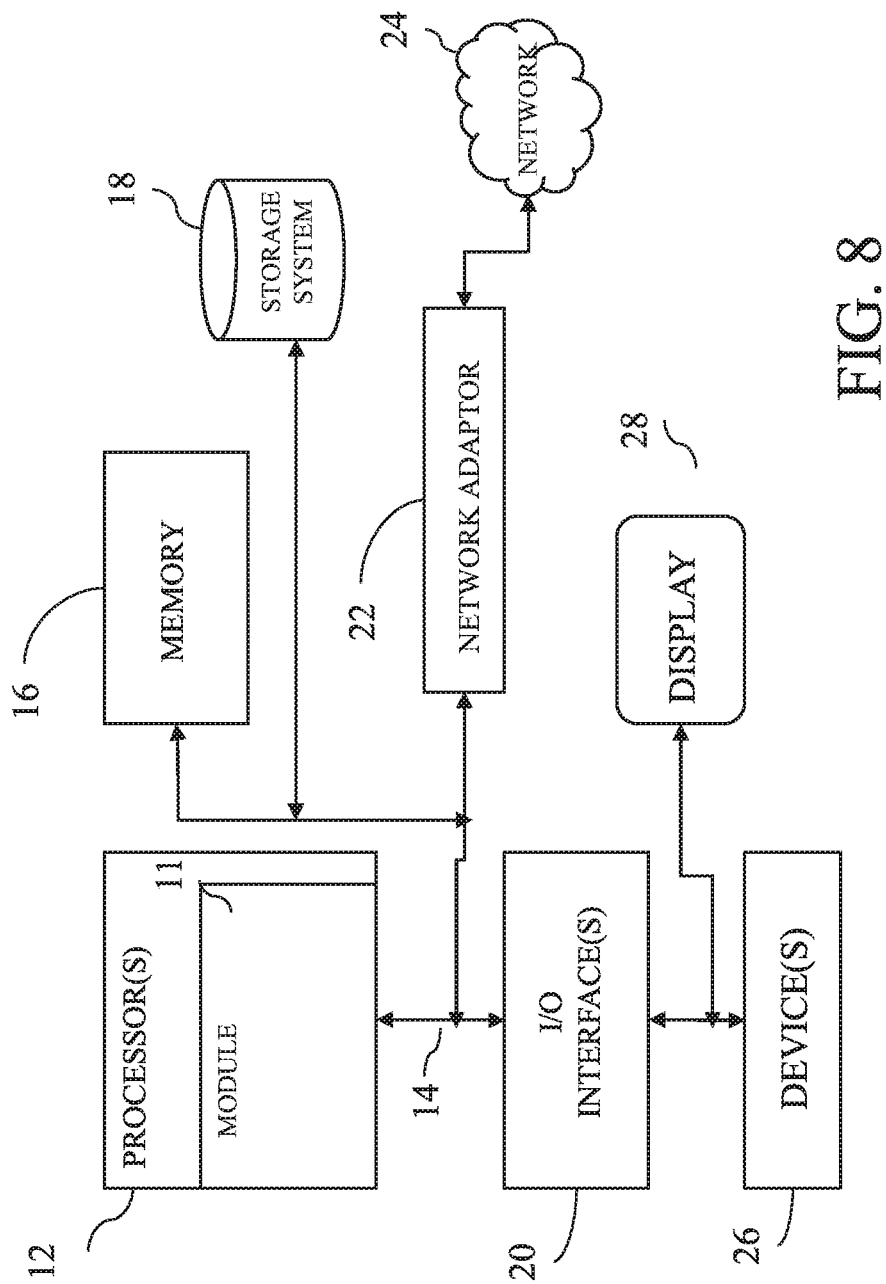
FIG. 8 illustrates a schematic of an example computer or processing system that may implement a reactant prediction system in one embodiment of the present disclosure.

FIG. 8 illustrates a schematic of an example computer or processing system that may implement customer differentiated order fulfillment assignment in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 8 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 11 that performs the methods described herein. The module 11 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a special purpose computer or machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer implemented method for determining at least one candidate reactant for a target compound, comprising:
    forming by a computer processor a graph of known reactants and known products, the graph comprising links between the known reactants and their known products;
    receiving by a computer processor the target compound;
    determining by a computer processor whether the graph includes the target compound and, if the graph does not include the target compound, adding the target compound as a new product to the graph;
    forming by a computer processor a matrix having values representing the known reactants, the known products and the target compound included in the graph;
    determining a similarity between the known reactants and the target compound and assigning a higher value in the matrix to one or more of the known reactants that are determined as being similar to the target compound, wherein the similarity between the known reactants and the target compound is based on a structural similarity or on a number of bond path similarities;
    factoring by a computer processor the graph to provide a matrix value for each of the known reactants; and
    determining by a computer processor whether there is at least one link in the graph between the target compound and at least one known reactant based on the matrix values, and if a link is determined, assigning the at least one known reactant as the at least one candidate reactant.

2. The method of claim 1, further comprising a step prior to the forming the graph step of receiving by a computer processor reaction data of a plurality of known reactants and known products.

3. The method of claim 1, wherein one or more known reactants are removed by a computer processor from the graph after the graph is formed because the one or more known reactants are below a threshold molecular weight or below a threshold molecular size.

4. The method of claim 1, wherein the matrix value for the one or more candidate reactants is modified by a computer processor based on at least one of availability of the reactant, costs of the reactant, reaction speed of the reactant, thermodynamic properties of the reactant, toxicity of the reactant and biological activity of the reactant.

5. The method of claim 1, wherein the computer implemented method is provided as a service in a cloud environment.

6. A system for determining at least one candidate reactant for a target compound, comprising:
    one or more storage devices;
    one or more hardware processors coupled to the one or more storage devices;
    one or more hardware processors operable to form a graph of known reactants and known products, the graph comprising links between the known reactants and their known products;
    one or more hardware processors operable to receive the target compound;
    one or more hardware processors operable to determine whether the graph includes the target compound and, if the graph does not include the target compound, adding the target compound as a new product to the graph;
    one or more hardware processors operable to form a matrix having values representing the known reactants, the known products and the target compound included in the graph;
    one or more hardware processors operable to determine a similarity between the known reactants and the target compound and assigning a higher value in the matrix to one or more of the portion of known reactants that are determined as being similar to the target compound, wherein the similarity between the known reactants and the target compound is based on a structural similarity or on a number of bond path similarities;
    one or more hardware processors operable to factor the graph to provide a matrix value for each of the known reactants; and
    one or more hardware processors operable to determine whether there is at least one link in the graph between the target compound and at least one known reactant based on the matrix values, and if a link is determined, assigning the at least one known reactant as the at least one candidate reactant.

7. The system of claim 6, further comprising one or more hardware processors operable to receive reaction data of a plurality of known reactants and known products.

8. The system of claim 6, wherein one or more known reactants are removed by the one or more hardware processors from the graph after the graph is formed because the one or more known reactants are below a threshold molecular weight or below a threshold molecular size.

9. The system of claim 6, wherein the matrix value for the one or more candidate reactants is modified by a computer processor based on at least one of availability of the reactant, costs of the reactant, reaction speed of the reactant, thermodynamic properties of the reactant, toxicity of the reactant and biological activity of the reactant.

10. A computer readable storage medium storing a program of instructions executable by a machine to perform a method for determining at least one candidate reactant for a target compound, the method comprising:
    forming by a computer processor a graph of known reactants and known products, the graph comprising links between the known reactants and their known products;
    receiving by a computer processor the target compound;
    determining by a computer processor whether the graph includes the target compound and, if the graph does not include the target compound, adding the target compound as a new product to the graph;

forming by a computer processor a matrix having values representing the known reactants, the known products and the target compound included in the graph;

determining a similarity between the known reactants and the target compound and assigning a higher value in the matrix to one or more of the known reactants that are determined as being similar to the target compound, wherein the similarity between the portion of the known reactants and the target compound is based on a structural similarity or on a number of bond path similarities;

factoring by a computer processor the graph to provide a matrix value for each of the known reactants; and determining by a computer processor whether there is at least one link in the graph between the target compound and at least one known reactant based on the matrix values, and if a link is determined, assigning the at least one known reactant as the at least one candidate reactant.

11. The computer readable storage medium of claim 10, wherein reaction data of a plurality of known reactants and known products are received by a computer processor.

12. The computer readable storage medium of claim 10, wherein one or more known reactants are removed by a computer processor from the graph after the graph is formed because the one or more known reactants are below a threshold molecular weight or below a threshold molecular size.

13. The computer readable storage medium of claim 10, wherein the matrix value for the one or more candidate reactants is modified by a computer processor based on at least one of availability of the reactant, costs of the reactant, reaction speed of the reactant, thermodynamic properties of the reactant, toxicity of the reactant and biological activity of the reactant.

* * * * *